United States Patent
Coulthard et al.

(10) Patent No.: US 10,265,441 B2
(45) Date of Patent: Apr. 23, 2019

(54) SYSTEM, METHOD, AND APPARATUS FOR REGULATING PRESSURE

(71) Applicant: KCI Licensing, Inc., San Antonio, TX (US)

(72) Inventors: Richard Daniel John Coulthard, Verwood (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 1208 days.

(21) Appl. No.: 14/024,066

(22) Filed: Sep. 11, 2013

(65) Prior Publication Data

US 2014/0100539 A1 Apr. 10, 2014

Related U.S. Application Data

(60) Provisional application No. 61/701,394, filed on Sep. 14, 2012.

(51) Int. Cl.
*A61M 1/00* (2006.01)

(52) U.S. Cl.
CPC ........ *A61M 1/0031* (2013.01); *A61M 1/0088* (2013.01); *A61M 2205/3341* (2013.01)

(58) Field of Classification Search
CPC combination set(s) only.
See application file for complete search history.

(56) References Cited

U.S. PATENT DOCUMENTS

| | | |
|---|---|---|
| 1,355,846 A | 10/1920 | Rannells |
| 2,419,795 A | 4/1947 | Saunders |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

Partial International Search Report for corresponding PCT/US2013/059248 dated Jan. 27, 2014.

(Continued)

*Primary Examiner* — Tatyana Zalukaeva
*Assistant Examiner* — Guy K Townsend

(57) ABSTRACT

Subject matter relating to pressure regulation is described. In one illustrative embodiment, an apparatus for regulating pressure may include a supply chamber, a control chamber, and a charging chamber. The supply chamber may have a supply port adapted for coupling to a supply lumen, and the control chamber may have a control port adapted for coupling to a feedback lumen. The charging chamber can be fluidly coupled to the supply chamber through a charging port. A regulator valve within the control chamber can operate to control fluid communication through the charging port based on a differential between pressure in the control chamber and a target pressure.

14 Claims, 14 Drawing Sheets

(56) References Cited

U.S. PATENT DOCUMENTS

| | | | |
|---|---|---|---|
| 3,084,691 A | 4/1963 | Stoner | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 3,875,941 A | 4/1975 | Adair | |
| 4,080,970 A | 3/1978 | Miller | |
| 4,096,853 A | 6/1978 | Weigand | |
| 4,098,434 A | 7/1978 | Uhlig | |
| 4,132,332 A | 1/1979 | Wassilieff | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,578,060 A | 3/1986 | Huck et al. | |
| 4,605,399 A | 8/1986 | Weston et al. | |
| 4,608,041 A | 8/1986 | Nielson | |
| 4,640,688 A | 2/1987 | Hauser | |
| 4,642,088 A | 2/1987 | Gunter | |
| 4,643,719 A | 2/1987 | Garth et al. | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,798,583 A | 1/1989 | Beck et al. | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,903,726 A * | 2/1990 | Martin | A61M 1/0031 137/495 |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 4,986,289 A | 1/1991 | Martin | |
| 4,986,298 A * | 1/1991 | Martin | A61M 1/0031 137/15.22 |
| 5,019,059 A | 5/1991 | Goldberg et al. | |
| 5,024,653 A | 6/1991 | Kohnke | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,226,877 A | 7/1993 | Epstein | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,304,129 A | 4/1994 | Forgach | |
| 5,318,548 A | 6/1994 | Filshie | |
| 5,342,376 A | 8/1994 | Ruff | |
| 5,344,415 A | 9/1994 | DeBusk et al. | |
| 5,358,494 A | 10/1994 | Svedman | |
| 5,419,768 A * | 5/1995 | Kayser | A61M 1/0031 128/205.19 |
| 5,437,622 A | 8/1995 | Carion | |
| 5,437,651 A | 8/1995 | Todd et al. | |
| 5,527,293 A | 6/1996 | Zamierowski | |
| 5,542,939 A | 8/1996 | Onodera et al. | |
| 5,549,584 A | 8/1996 | Gross | |
| 5,556,375 A | 9/1996 | Ewall | |
| 5,592,948 A | 1/1997 | Gatten | |
| 5,607,388 A | 3/1997 | Ewall | |
| 5,636,643 A | 6/1997 | Argenta et al. | |
| 5,645,081 A | 7/1997 | Argenta et al. | |
| 5,645,540 A | 7/1997 | Henniges et al. | |
| 5,714,696 A | 2/1998 | Yeamans | |
| 5,819,990 A | 10/1998 | Cimentepe et al. | |
| 5,827,246 A | 10/1998 | Bowen | |
| 5,830,198 A | 11/1998 | Henniges et al. | |
| 6,024,120 A | 2/2000 | Yam | |
| 6,071,267 A | 6/2000 | Zamierowski | |
| 6,135,116 A | 10/2000 | Vogel et al. | |
| 6,174,306 B1 | 1/2001 | Fleischmann | |
| 6,241,747 B1 | 6/2001 | Ruff | |
| 6,261,276 B1 | 7/2001 | Reitsma | |
| 6,287,316 B1 | 9/2001 | Agarwal et al. | |
| 6,345,623 B1 | 2/2002 | Heaton et al. | |
| 6,447,491 B1 * | 9/2002 | Lord | A61M 1/0031 604/317 |
| 6,485,007 B1 | 11/2002 | Duelli | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,656,149 B2 | 12/2003 | Ladd | |
| 6,745,765 B2 | 6/2004 | Kullik et al. | |
| 6,749,592 B2 | 6/2004 | Lord | |
| 6,814,079 B2 | 11/2004 | Heaton et al. | |
| 7,255,127 B2 * | 8/2007 | Davidson | G05D 16/103 137/495 |
| 7,625,362 B2 | 12/2009 | Boehringer et al. | |
| 7,776,008 B2 | 8/2010 | Renz et al. | |
| 7,857,806 B2 | 12/2010 | Karpowicz et al. | |
| 8,007,257 B2 | 8/2011 | Heaton | |
| 8,864,748 B2 * | 10/2014 | Coulthard | A61M 1/0088 602/42 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0040687 A1 | 2/2003 | Boynton et al. | |
| 2004/0064132 A1 | 4/2004 | Boehringer et al. | |
| 2004/0243105 A1 | 12/2004 | Swan et al. | |
| 2005/0004534 A1 | 1/2005 | Lockwood et al. | |
| 2005/0087556 A1 | 4/2005 | Signoriri | |
| 2005/0197639 A1 | 9/2005 | Mombrinie | |
| 2006/0025727 A1 | 2/2006 | Boehringer et al. | |
| 2006/0079852 A1 | 4/2006 | Bubb et al. | |
| 2006/0127233 A1 | 6/2006 | Sasayama et al. | |
| 2006/0129137 A1 | 6/2006 | Lockwood et al. | |
| 2006/0216171 A1 | 9/2006 | Hernandez | |
| 2007/0179460 A1 * | 8/2007 | Adahan | A61M 1/0066 604/319 |
| 2007/0214692 A1 | 9/2007 | Ferrara | |

(56) References Cited

U.S. PATENT DOCUMENTS

| | | | |
|---|---|---|---|
| 2008/0183156 A1 | 7/2008 | Yoo | |
| 2008/0306456 A1 | 12/2008 | Riesinger | |
| 2009/0012501 A1 | 1/2009 | Boehringer et al. | |
| 2009/0125004 A1 | 5/2009 | Shen et al. | |
| 2009/0275922 A1* | 11/2009 | Coulthard | A61M 1/0088 604/543 |
| 2009/0326488 A1 | 12/2009 | Budig et al. | |
| 2011/0077605 A1 | 3/2011 | Karpowicz et al. | |
| 2012/0226247 A1 | 9/2012 | Danei et al. | |
| 2014/0100539 A1* | 4/2014 | Coulthard | A61M 1/0088 604/319 |
| 2014/0188061 A1* | 7/2014 | Locke | A61M 1/0049 604/321 |
| 2015/0094673 A1* | 4/2015 | Pratt | A61M 1/0088 604/318 |
| 2015/0094674 A1* | 4/2015 | Pratt | A61F 13/00068 604/318 |

FOREIGN PATENT DOCUMENTS

| | | |
|---|---|---|
| AU | 755496 | 2/2002 |
| CA | 2005436 | 6/1990 |
| CN | 2142728 Y | 9/1993 |
| CN | 1571682 A | 1/2005 |
| CN | 2745582 Y | 12/2005 |
| CN | 2829771 Y | 10/2006 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1406142 A2 | 9/2003 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| GB | 2431351 A | 4/2007 |
| JP | 60050296 A | 3/1985 |
| JP | 4129536 | 4/1992 |
| SG | 71559 | 4/2002 |
| WO | 80/02182 | 10/1980 |
| WO | 87/04626 | 8/1987 |
| WO | 89/01657 A1 | 2/1989 |
| WO | 89/07459 A1 | 8/1989 |
| WO | 90/010424 | 9/1990 |
| WO | 93/09727 | 5/1993 |
| WO | 94/020041 | 9/1994 |
| WO | 96/05873 | 2/1996 |
| WO | 96/35401 A1 | 11/1996 |
| WO | 97/18007 | 5/1997 |
| WO | 99/13793 | 3/1999 |
| WO | 2007013064 A1 | 2/2007 |
| WO | 2009086580 A1 | 7/2009 |
| WO | 2009135171 A2 | 11/2009 |

OTHER PUBLICATIONS

International Search Report and Written Opinion for corresponding PCT/US2013/059248 dated Sep. 1, 2014.
N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic

(56) References Cited

OTHER PUBLICATIONS

Wound Care, edited by D. Krasner (Health Management Publications, Inc., King of Prussia, PA 1990), pp. 240-246.

G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

Japanese Application 2015-532020 corresponding to First Office Action, dated Jun. 13, 2017.

\* cited by examiner

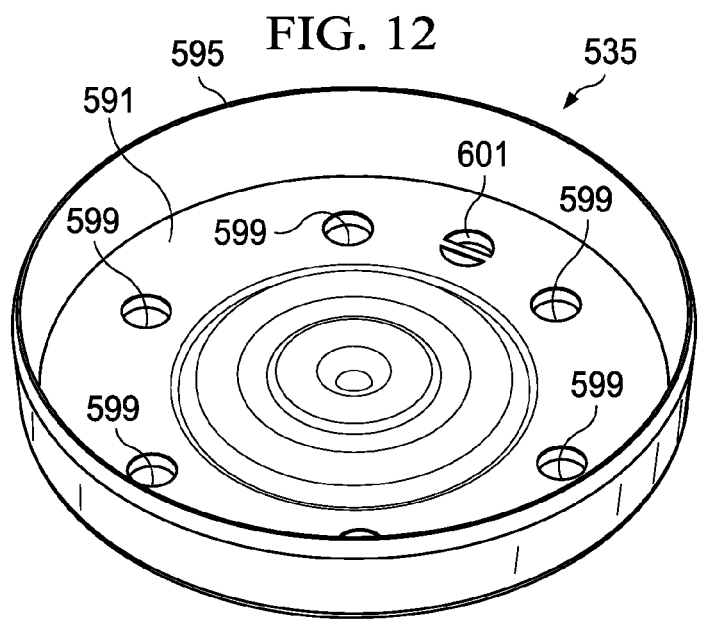
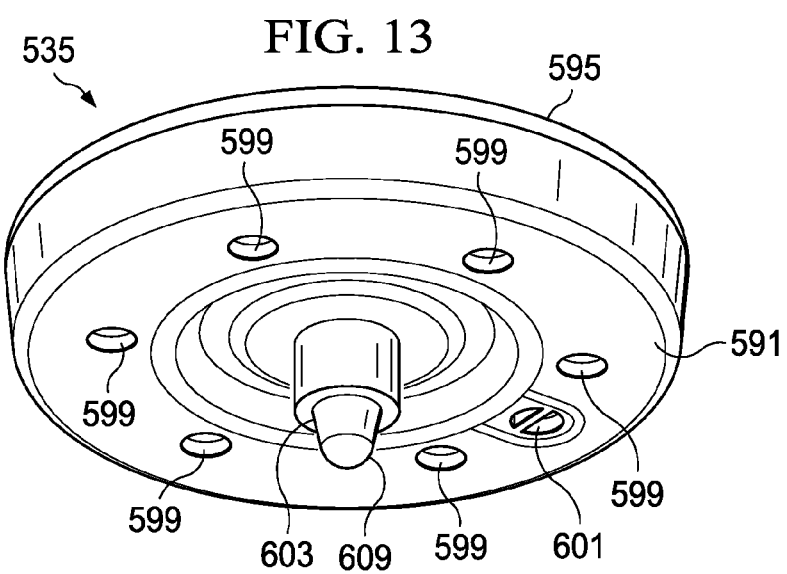

SYSTEM, METHOD, AND APPARATUS FOR REGULATING PRESSURE

RELATED APPLICATION

The present invention claims the benefit, under 35 USC § 119(e), of the filing of U.S. Provisional Patent Application Ser. No. 61/701,394, entitled "SYSTEM, METHOD, AND APPARATUS FOR REGULATING PRESSURE," filed 14 Sep. 2012, which is incorporated herein by reference for all purposes

TECHNICAL FIELD

The subject matter described herein relates generally to regulating pressure. In more particular embodiments, the subject matter relates to regulating pressure for reduced-pressure therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure is commonly referred to as "reduced-pressure therapy," but may also be known by other names, including "negative pressure wound therapy" and "vacuum therapy," for example. Reduced-pressure therapy may provide a number of benefits, including migration of epithelial and subcutaneous tissues, improved blood flow, and microdeformation of tissue at a wound site. Together, these benefits can increase development of granulation tissue and reduce healing times.

While the clinical benefits of reduced-pressure therapy are widely known, the cost and complexity of reduced-pressure therapy can be a limiting factor in its application, and the development and operation of reduced-pressure systems, components, and processes continues to present significant challenges to manufacturers, healthcare providers, and patients.

SUMMARY

Illustrative embodiments of systems, methods, and apparatuses for regulating pressure are described below. One such illustrative embodiment may be described as a reduced-pressure treatment system, which may include a dressing, a supply chamber, a control chamber, a charging chamber. The supply chamber can be fluidly coupled to the dressing through a supply lumen, and the control chamber can be fluidly coupled to the dressing through a feedback lumen. The charging chamber can be fluidly coupled to the supply chamber through a port. A regulator valve within the control chamber controls fluid communication through the port based on a differential between a control pressure in the control chamber and a therapy pressure.

Another illustrative embodiment relates to a method for regulating pressure, such as a therapeutic pressure. One such method may include placing a manifold in a sealed environment proximate to a tissue site, fluidly coupling the manifold to a supply chamber through a supply lumen, and fluidly coupling the manifold to a control chamber through a control lumen. The supply chamber may also be fluidly coupled to a charging chamber, and a charging pressure in the charging chamber can be reduced below a therapy pressure. Fluid communication between the supply chamber and the charging chamber can be regulated based on a differential between a control pressure in the control chamber and the therapy pressure. A regulated supply pressure from the supply chamber can be delivered to the manifold.

Yet another illustrative embodiment relates to an apparatus for regulating pressure. In one form, such an apparatus may include a supply chamber, a control chamber, and a charging chamber. The supply chamber may have a supply port adapted for coupling to a supply lumen, and the control chamber may have a control port adapted for coupling to a feedback lumen. The charging chamber can be fluidly coupled to the supply chamber through a charging port. A regulator valve within the control chamber can operate to control fluid communication through the charging port based on a differential between pressure in the control chamber and a target pressure.

Another illustrative embodiment of an apparatus for regulating pressure may include a lower housing having an end wall and a side wall. A first piston opposite the end wall of the lower housing may be engaged to the side wall of the lower housing to define a charging chamber within the lower housing. A partition in the first piston can separate a lower bowl from an upper bowl. A charging spring may be engaged to the first piston and the end wall of the lower housing. A charging port through the first piston can provide fluid communication between the charging chamber and a supply chamber defined by the partition and the lower bowl. An upper housing may have a floor and a side wall, wherein the side wall of the upper housing can be coupled to the side wall of the lower housing. A control chamber may be generally defined by the upper bowl and the floor of the upper housing. A second piston opposite the upper bowl may be engaged to the side wall of the lower housing, wherein the second piston can divide the control chamber into an ambient pressure region and a control pressure region. A valve body may extend through an aperture in the partition into the supply chamber, the valve body having a first end coupled to the second piston and a second end disposed adjacent to the charging port in the supply chamber. A regulator spring can engage the valve body between the charging port and the second piston. A multi-channel port can be exposed externally through the upper housing, and the multi-channel port can provide a supply port fluidly coupled to the supply chamber and a control port fluidly coupled to the control pressure region of the control chamber. The multi-channel port can be coupled with a multi-lumen tube.

Other features and advantages will become apparent with reference to the drawings and detailed description that follow.

BRIEF DESCRIPTION OF THE DRAWINGS

FIG. 12 is a top-rear perspective view of a seal of the vacuum pump of FIG. 5;

FIG. 13 is a bottom-rear perspective view of the seal of FIG. 12;

DETAILED DESCRIPTION

New and useful systems, methods, and apparatuses associated with regulating pressure are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

The example embodiments may also be described herein in the context of a reduced-pressure therapy applications, but many of the features and advantages are readily applicable to other environments and industries. Spatial relationships between various elements or to the spatial orientation of various elements may be described as depicted in the attached drawings. In general, such relationships or orientations assume a frame of reference consistent with or relative to a patient in a position to receive reduced-pressure therapy. However, as should be recognized by those skilled in the art, this frame of reference is merely a descriptive expedient rather than a strict prescription.

Figure 1:
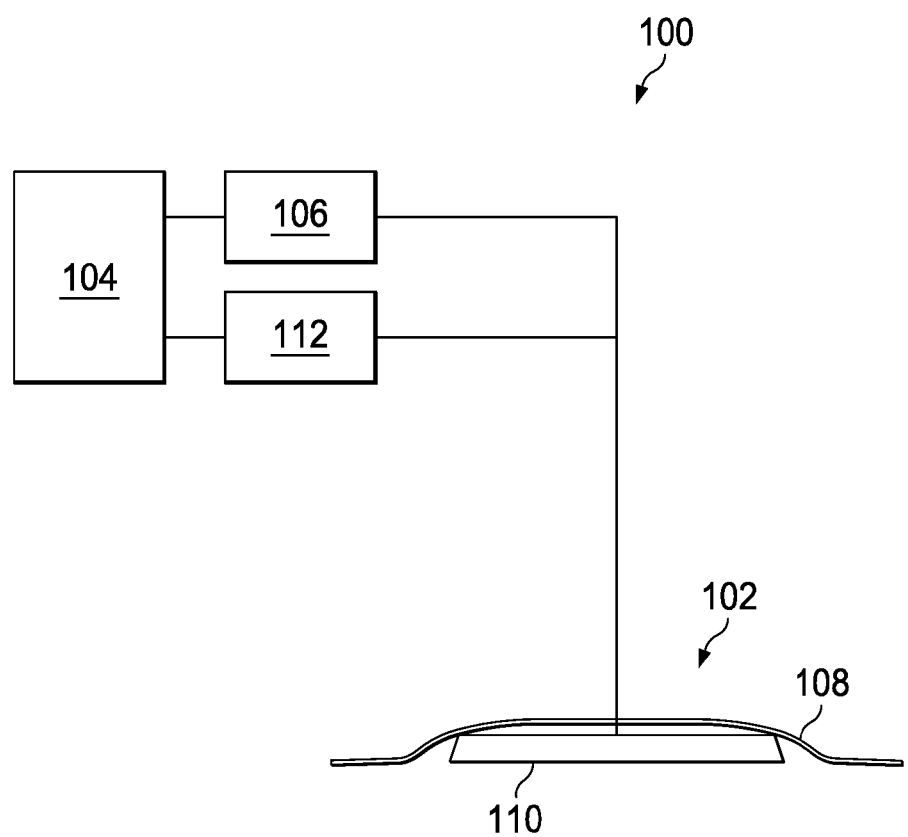
FIG. 1 is a functional block diagram of an example embodiment of a reduced-pressure therapy system that can regulate therapeutic pressure in accordance with this specification.

FIG. 1 is a simplified functional block diagram of an example embodiment of a reduced-pressure therapy system 100 that can regulate therapeutic pressure in accordance with this specification. As illustrated, reduced-pressure therapy system 100 may include a dressing 102 fluidly coupled to a reduced-pressure source 104. A regulator or controller, such as regulator 106, may also be fluidly coupled to dressing 102 and reduced-pressure source 104. Dressing 102 generally includes a drape, such as drape 108, and a manifold, such as pressure distribution manifold 110. Reduced-pressure therapy system 100 may also include a fluid container, such as container 112, coupled to dressing 102 and reduced-pressure source 104.

In general, components of reduced-pressure therapy system 100 may be coupled directly or indirectly. For example, reduced-pressure source 104 may be directly coupled to regulator 106 and indirectly coupled to dressing 102 through regulator 106. Components may be fluidly coupled to each other to provide a path for transferring fluids (i.e., liquid and/or gas) between the components. In some embodiments, components may be fluidly coupled with a tube, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, pressure distribution manifold 110 may be placed within, over, on, or otherwise proximate to a tissue site. Drape 108 may be placed over pressure distribution manifold 110 and sealed to tissue proximate to the tissue site. The tissue proximate to the tissue site is often undamaged epidermis peripheral to the tissue site. Thus, dressing 102 can provide a sealed therapeutic environment proximate to a tissue site, substantially isolated from the external environment, and reduced-pressure source 104 can reduce the pressure in the sealed therapeutic environment. Reduced pressure applied uniformly through pressure distribution manifold 110 in the sealed therapeutic environment can induce macrostrain and microstrain in the tissue site, as well as remove exudates and other fluids from the tissue site, which can be collected in container 112 and disposed of properly.

The fluid mechanics of using a reduced-pressure source to reduce pressure in another component or location, such as within a sealed therapeutic environment, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

In general, exudates and other fluids flow toward lower pressure along a fluid path. This orientation is generally presumed for purposes of describing various features and components of reduced-pressure therapy systems herein. Thus, the term "downstream" typically implies something in a fluid path relatively closer to a reduced-pressure source, and conversely, the term "upstream" implies something relatively further away from a reduced-pressure source. Similarly, it may be convenient to describe certain features in terms of fluid "inlet" or "outlet" in such a frame of reference. However, the fluid path may also be reversed in some applications, such as by substituting a positive-pressure source, and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of tissue that are not necessarily wounded or defective, but are instead areas in which it may be desired to add or promote the growth of additional tissue. For example, reduced pressure may be used in certain tissue areas to grow additional tissue that may be harvested and transplanted to another tissue location.

"Reduced pressure" generally refers to a pressure less than a local ambient pressure, such as the ambient pressure in a local environment external to a sealed therapeutic environment provided by dressing 102. In many cases, the local ambient pressure may also be the atmospheric pressure in a patient's vicinity. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

A reduced-pressure source, such as reduced-pressure source 104, may be a reservoir of air at a reduced pressure, or may be a manual or electrically-powered device that can reduced the pressure in a sealed volume, such as a vacuum pump, a suction pump, a wall suction port available at many healthcare facilities, or a micro-pump, for example. The reduced-pressure source may be housed within or used in conjunction with other components, such as sensors, processing units, alarm indicators, memory, databases, software, display devices, or user interfaces that further facilitate reduced-pressure therapy. While the amount and nature of reduced pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

Pressure distribution manifold 110 can generally be adapted to contact a tissue site. Pressure distribution manifold 110 may be partially or fully in contact with the tissue site. If the tissue site is a wound, for example, pressure distribution manifold 110 may partially or completely fill the wound, or may be placed over the wound. Pressure distribution manifold 110 may take many forms, and may be many sizes, shapes, or thicknesses depending on a variety of factors, such as the type of treatment being implemented or the nature and size of a tissue site. For example, the size and shape of pressure distribution manifold 110 may be adapted to the contours of deep and irregular shaped tissue sites.

More generally, a manifold is a substance or structure adapted to distribute reduced pressure to or remove fluids from a tissue site, or both. In some embodiments, though, a manifold may also facilitate delivering fluids to a tissue site, if the fluid path is reversed or a secondary fluid path is provided, for example. A manifold may include flow channels or pathways that distribute fluids provided to and removed from a tissue site around the manifold. In one illustrative embodiment, the flow channels or pathways may be interconnected to improve distribution of fluids provided to or removed from a tissue site. For example, cellular foam, open-cell foam, porous tissue collections, and other porous material such as gauze or felted mat generally include structural elements arranged to form flow channels. Liquids, gels, and other foams may also include or be cured to include flow channels.

In one illustrative embodiment, pressure distribution manifold 110 may be a porous foam material having interconnected cells or pores adapted to uniformly (or quasi-uniformly) distribute reduced pressure to a tissue site. The foam material may be either hydrophobic or hydrophilic. In one non-limiting example, pressure distribution manifold 110 may be an open-cell, reticulated polyurethane foam such as GranuFoam® dressing available from Kinetic Concepts, Inc. of San Antonio, Tex.

In some embodiments, such as embodiments in which pressure distribution manifold 110 may be made from a hydrophilic material, pressure distribution manifold 110 may also wick fluid away from a tissue site while continuing to distribute reduced pressure to the tissue site. The wicking properties of pressure distribution manifold 110 may draw fluid away from a tissue site by capillary flow or other wicking mechanisms. An example of a hydrophilic foam is a polyvinyl alcohol, open-cell foam such as V.A.C. White-Foam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

Pressure distribution manifold 110 may further promote granulation at a tissue site if pressure within a sealed therapeutic environment is reduced. For example, any or all of the surfaces of pressure distribution manifold 110 may have an uneven, coarse, or jagged profile that can induce microstrains and stresses at a tissue site if reduced pressure is applied through pressure distribution manifold 110.

In one example embodiment, pressure distribution manifold 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. Pressure distribution manifold 110 may further serve as a scaffold for new cell-growth, or a scaffold material may be used in conjunction with pressure distribution manifold 110 to promote cell-growth. In general, a scaffold material may be a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Drape 108 is an example of a sealing member. A sealing member may be constructed from a material that can provide a fluid seal between two environments or components, such as between a therapeutic environment and a local external environment. The sealing member may be, for example, an impermeable or semi-permeable, elastomeric material that can provide a seal adequate to maintain a reduced pressure at a tissue site for a given reduced-pressure source. For semi-permeable materials, the permeability generally should be low enough that a desired reduced pressure may be maintained. An attachment device may be used to attach a sealing member to an attachment surface, such as undamaged epidermis, a gasket, or another sealing member. The attachment device may take many forms. For example, an attachment device may be a medically-acceptable, pressure-sensitive adhesive that extends about a periphery, a portion, or an entire sealing member. Other example embodiments of an attachment device may include a double-sided tape, paste, hydrocolloid, hydrogel, silicone gel, organogel, or an acrylic adhesive.

Container 112 is representative of a container, canister, pouch, or other storage component that can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with reduced-pressure therapy.

In general, reduced-pressure therapy can be beneficial for wounds of all severity, but the cost and complexity of reduced-pressure therapy systems often limit the application of reduced-pressure therapy to large, highly-exudating wounds present on patients undergoing acute or chronic care, as well as other severe wounds that are not readily susceptible to healing without application of reduced pressure. For example, the complexity of conventional reduced-pressure therapy systems can limit the ability of a person with little or no specialized knowledge from administering reduced-pressure therapy. The size of many reduced-pressure therapy systems may also impair mobility. Many reduced-pressure therapy systems also require careful cleaning after each treatment, and may require electrical components or other powered devices to supply the reduced pressure for treatment. Although some reduced-pressure therapy systems deploy a purely mechanical method for reducing pressure, such systems have been unable to provide adequate control of the level of reduced pressure.

Reduced-pressure therapy system 100 may overcome these shortcomings and others by providing mechanical regulation of therapeutic pressure. In one example embodiment, reduced-pressure therapy system 100 may include a manually-actuated hand pump for reducing pressure. A valve can regulate pressure down to a mechanically predetermined target pressure and supply this pressure to a sealed therapeutic environment proximate a tissue site via a supply lumen, and a feedback lumen can be fluidly connected to the valve within the pump. Pressure transmitted by the feedback lumen can control the action of the valve, which controls the pressure delivered to the tissue site. Thus, such an embodiment of reduced-pressure therapy system 100 can accurately control the pressure within the sealed therapeutic environment, including offsetting blockage that may occur in a dressing or storage system by further reducing the supplied pressure.

Figure 2A:
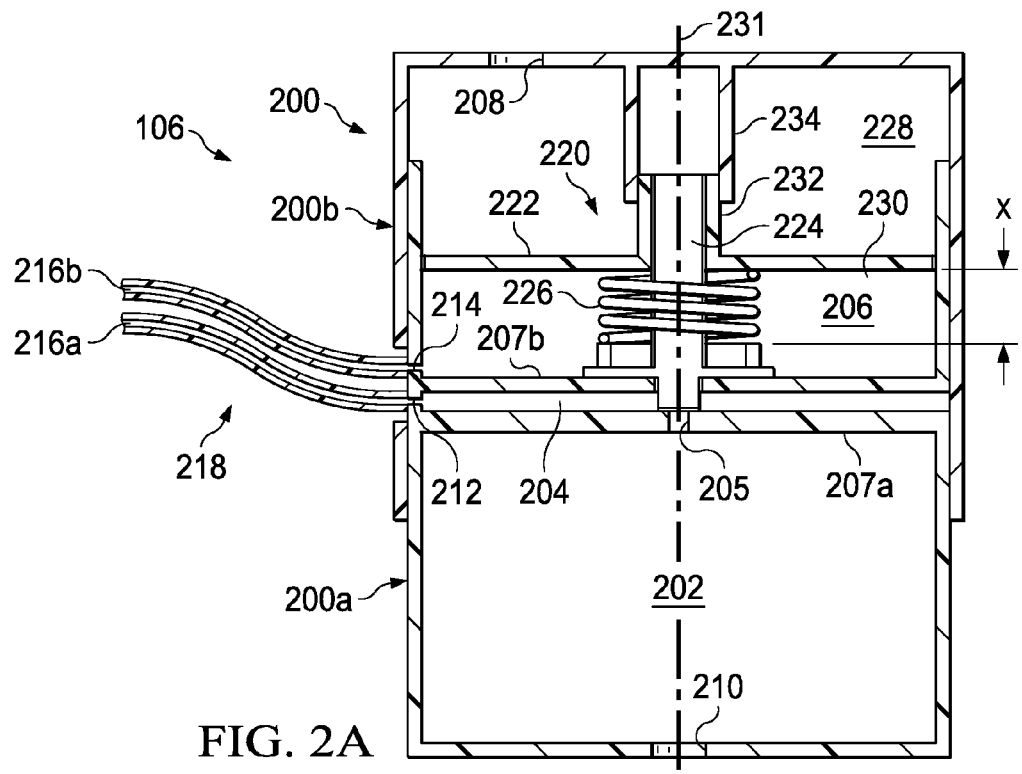
FIGS. 2A-2B are schematic cross-sections of an example embodiment of a regulator in the reduced-pressure therapy system.
Figure 2B:
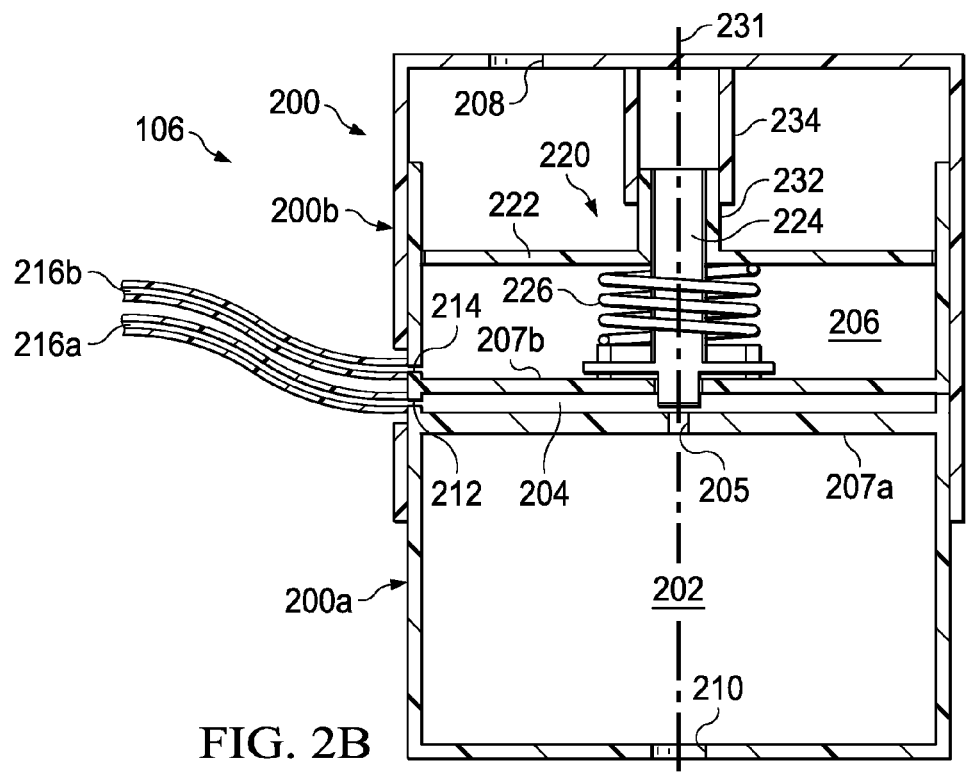

FIGS. 2A-2B are simplified schematic cross-sections of an example embodiment of an apparatus for regulating pressure, such as regulator 106. In this example embodiment, regulator 106 can include a housing 200 having a charging chamber 202, a supply chamber 204, and a control chamber 206. Charging chamber 202 may be fluidly coupled to supply chamber 206 through a conduit, passage, or port, such as charging port 205. A port 208 can provide fluid communication between control chamber 206 and a source of ambient pressure. Charging chamber 202 may also include a port, such as port 210, which can be fluidly coupled to a source of reduced pressure, such as reduced-pressure source 104. The charging chamber 202 may be adapted to receive reduced pressure from a device that can be manually-actuated, or alternatively that can be powered by electrical or other means.

A supply port 212 may fluidly connect supply chamber 204 to a dressing, such as dressing 102 in FIG. 1, and a control port 214 may fluidly couple control chamber 206 to the dressing. For example, in one embodiment, a first lumen such as supply lumen 216a may fluidly connect supply port 212 and supply chamber 204 to a dressing, and a second lumen such as feedback lumen 216b may fluidly couple control port 214 and control chamber 206 to the dressing. In some embodiments, the first lumen and the second lumen may be disposed within a single multi-lumen tube, such as tube 218. In other embodiments, more than one tube may be used to couple a dressing to supply port 212 and control port 214.

A regulator valve 220 can be operably associated with charging port 205 to regulate fluid communication between the charging chamber 202 and supply chamber 204. In some embodiments, regulator valve 220 may include a piston, a valve body, and an elastic member. A piston can be a flexible or movable barrier, for example, illustrated in FIGS. 2A-2B as piston 222. A valve body can be, for example, a generally rigid structure having a first end coupled to, adjoining, abutting, or otherwise engaging the piston, and movable with the piston. A second end of the valve body can be generally sized and shaped to engage and/or seal charging port 205. The valve body in FIGS. 2A-2B is illustrated as stem 224. As illustrated, stem 224 may extend through a partition into supply chamber 204. An elastic member, represented in FIGS. 2A-2B as regulator spring 226, can be a spring, rubber, or other elastic structure, for example, generally disposed between piston 222 and charging port 205. In FIGS. 2A-2B, for example, regulator spring 226 can be disposed within control chamber 206, but may be disposed in supply chamber 204 in other embodiments. Regulator spring 226 in this embodiment can be a coil spring and coaxial with stem 224, for example, which biases piston 222 against ambient pressure 228 in control chamber 206.

In some embodiments, housing 200 may be formed from two components. For example, housing 200 may be formed from a lower housing 200a and a upper housing 200b, as illustrated in FIGS. 2A-2B. Lower housing 200a and upper housing 200b in this example each include an end wall, a side wall adjoining the end wall, and an open end opposite the end wall. Either lower housing 200a or upper housing 200b may have an outside dimension less than an inside dimension of the other so that one may be inserted into the other to form a structure that provides a substantially closed interior. In some embodiments, lower housing 200a and upper housing 200b may be engaged to allow relative movement between them. In more particular embodiments, lower housing 200a and upper housing 200b may each have cylindrical side walls and rounded end walls.

Charging chamber 202 may be generally defined by adjoining walls of housing 200, such as an end wall of housing 200, a side wall or walls of housing 200, and a partition within housing 200, such as chamber wall 207a. Supply chamber 204 may also be generally defined by adjoining walls within housing 200. For example, supply chamber 204 in FIGS. 2A-2B can be generally defined by chamber wall 207a, a side wall or walls of housing 200, and another partition, such as chamber wall 207b. Control chamber 206 may be similarly described, for example, as a chamber defined by chamber wall 207b, the side wall or walls of housing 200, and another end wall of housing 200. Thus, in this example embodiment, charging chamber 202 and supply chamber 204 may have a common wall (i.e., chamber wall 207a); supply chamber 204 and control chamber 206 may have a common wall (i.e., chamber wall 207b);

charging chamber 202 and supply chamber 204 can be fluidly isolated from each other except through charging port 205; charging chamber 202 and supply chamber 204 can be fluidly isolated from the ambient environment; and control chamber 206 can be fluidly isolated from charging chamber 202 and supply chamber 204.

Regulator valve 220 in this example can be disposed partially within control chamber 206 and partially within supply chamber 204, with circumferential edges of piston 222 abutting or engaging the side wall or walls of control chamber 206. The interface between piston 222 and the walls of control chamber 206 may also provide a fluid seal, dividing control chamber 206 into a region of ambient pressure 228 and a region of control pressure 230. However, regulator valve 220 may also reciprocate within control chamber 206 while maintaining the fluid seal. For example, regulator valve 220 may additionally include flexible o-rings disposed between piston 222 and the side wall of control chamber 206, and the o-rings may be lubricated so that regulator valve 220 can reciprocate within control chamber 206.

In operation, pressure in supply chamber 204 can be distributed to a remote chamber, environment, or other location through supply port 212. For example, pressure in supply chamber 204 may be distributed to a controlled environment, such as a sealed therapeutic environment associated with reduced-pressure therapy system 100. Control pressure 230 in control chamber 206 can be equalized with the pressure in the remote location through control port 214. In reduced-pressure therapy applications, control pressure 230 should be less than ambient pressure 228, resulting in a pressure differential across regulator valve 220. To simplify further description, the force on regulator valve 220 resulting from the pressure differential on opposing sides of piston 222 may be referred to as a "differential force." Regulator spring 226 also generally exerts a force on regulator valve 220. In expected operating ranges, the force of regulator spring 226 is directly proportional to the spring constant of regulator spring 226 and to a displacement X (i.e., displacement from a state of equilibrium) of the ends of regulator spring 226. Thus, if control pressure 230 is less than ambient pressure 228, the differential force on piston 222 tends to compress regulator spring 226 and, consequently, the force of regulator spring 226 opposes the differential force. The differential force and the force of regulator spring 226 can be combined to determine a net force acting on regulator valve 220. The net force can cause regulator valve 220 to move reciprocally within control chamber 206, such as along a central axis 231 aligned with charging port 205.

Regulator spring 226 may be selected, adjusted, modified, tuned, or otherwise calibrated so that control pressure 230 must drop below a threshold value (such as a target pressure) before the net force can move regulator valve 220 into a position that closes charging port 205. In some embodiments, for example, piston 222 may rotate within housing 200 to adjust the compression of regulator spring 226. In the embodiment illustrated in FIGS. 2A-2B, piston 222 includes a boss 232 that can be rigidly mated with a sleeve 234 of upper housing 200b, and stem 224 may be threaded or have a threaded portion engaged to boss 232. Stem 224 may be locked radially with housing 200 with a keyed feature. In such embodiments, piston 222 and upper housing 234 are generally locked radially and compression of regulator spring 226 may be adjusted by rotating upper housing 200b, which can cause piston 222 to rotate relative to stem 224. The change in compression of regulator spring 226 results in a change to the force of regulator spring 226 acting on regulator valve 220, and thus a change in the threshold value of control pressure 230 needed to actuate regulator valve 220. In many applications, this threshold value of control pressure 230 should generally correlate to a target pressure prescribed for reduced-pressure therapy, and may be referred to herein as the "therapy pressure" or "therapeutic pressure." Thus, in some embodiments, the therapy pressure may be adjusted by rotating upper housing 200b. In yet more particular embodiments, upper housing 200b may be calibrated to indicate various levels of therapy pressure.

Thus, charging chamber 202 may be charged and the pressure in the therapeutic environment may be controlled based on a differential between the therapy pressure and control pressure 230, by balancing the force of regulator spring 226 and the differential force (i.e., control pressure 230 on one side of piston 222 against ambient pressure 228 on an opposing side of piston 222). For reduced-pressure therapy applications, charging chamber 202 may be charged to a pressure lower than the therapy pressure. In one embodiment, for example, the desired therapy pressure may be about −125 mm Hg and pressure in charging chamber 202 may be reduced to a pressure of about −150 mm Hg.

If regulator valve 220 is calibrated to a particular therapy pressure and control pressure 230 is higher than the therapy pressure, the force of regulator spring 226 should exceed the differential force and the net force should actuate regulator valve 220, moving regulator valve 220 into an open position (see FIG. 2B) in which stem 224 disengages from (i.e., opens) charging port 205. Pressure between charging chamber 202 and supply chamber 204 can equalize through open charging port 205. As the pressure in charging chamber 202 and supply chamber 204 continues to equalize, the pressure in supply chamber 204 continues to decrease. Unless there is a complete blockage in the fluid path between supply chamber 204 and the therapeutic environment, pressure in the therapeutic environment also decreases and equalizes with the pressure in supply chamber 204 through supply lumen 216a. And unless there is a complete obstruction in the fluid path between the therapeutic environment and control chamber 206, control pressure 230 also decreases and equalizes with the pressure in the therapeutic environment through feedback lumen 216b. As control pressure 230 decreases and approaches the therapy pressure, the differential force increases until it exceeds the force of regulator spring 226, causing stem 224 to engage (i.e., close) charging port 205, which can substantially reduce or prevent fluid communication between charging chamber 202 and supply chamber 204 through charging port 205, as illustrated in FIG. 2A. Charging port 205 generally remains open, though, until control pressure 230 is less than or substantially equal to the therapy pressure. Advantageously, regulator valve 220 can keep charging port 205 open to compensate for pressure drops and partial blockages, particularly in the fluid path between supply chamber 204 and a controlled environment, because pressure in the controlled environment can be directly measured by feedback lumen 216b.

Figure 3A:
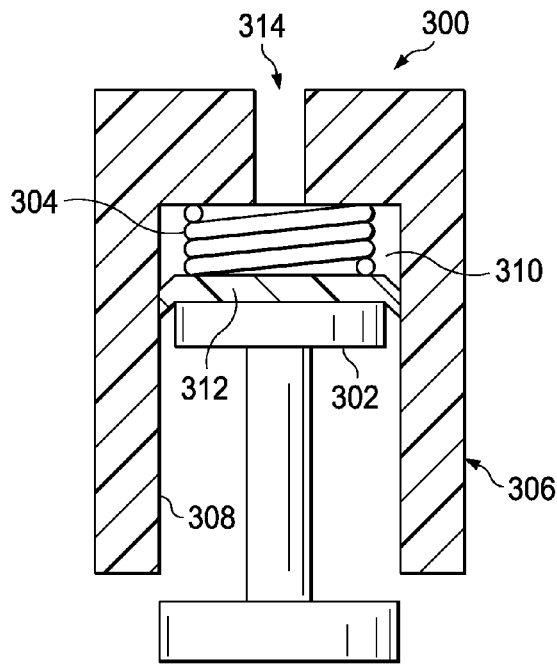
FIGS. 3A-3B are a cross-section of an example embodiment of a piston-driven pump in the reduced-pressure therapy system.
Figure 3B:
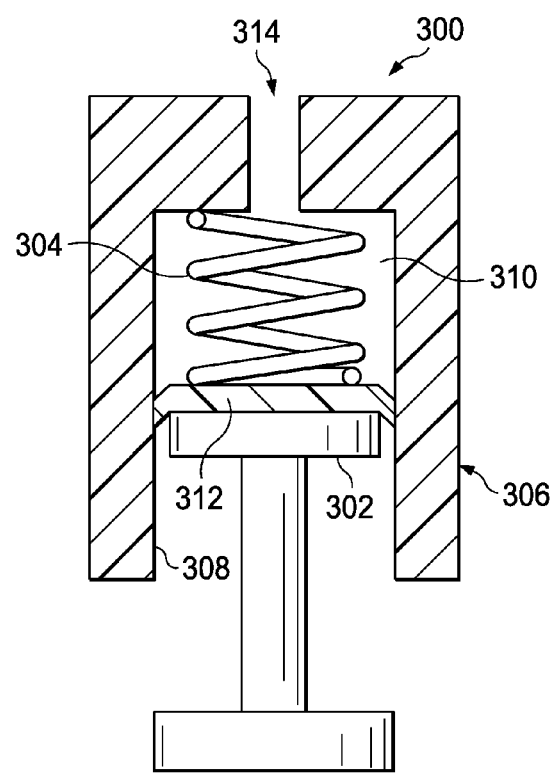

Referring to FIGS. 3A-3B, a cross-section of an example embodiment of a piston-driven pump 300 is illustrated. Piston-driven pump 300 may, for example, produce reduced pressure for a chamber such as charging chamber 202. Piston-driven pump 300 generally includes a piston 302, a piston spring 304, and a housing 306. Piston 302 can be disposed within a cavity of housing 306, such as a cylinder 308. A sealed portion of cylinder 308, such as vacuum chamber 310, may be disposed between piston 302 and an opposing end of cylinder 308. As illustrated, a seal 312 may be disposed within cylinder 308 to fluidly seal vacuum chamber 310 from the remainder of cylinder 308. A port 314 in housing 306 may allow fluid to flow out of vacuum chamber 310. For example, port 314 may be fluidly coupled to port 210 to allow fluid to flow between vacuum chamber 310 and charging chamber 202. In some embodiments, port 314 and port 210 may be the same port.

A check valve may be used to allow unidirectional flow out of vacuum chamber 310. For example, an o-ring may seal piston 302 against the side wall of cylinder 308 and a ball check valve in piston 302 may allow fluid to flow out of vacuum chamber 310 through a port in piston 302. In other embodiments, such as the embodiment illustrated in FIGS. 3A-3B, a flexible seal 312 may be disposed within cylinder 308 to fluidly seal vacuum chamber 310. Pressure on a compression stroke creates a pressure differential that can cause seal 312 to flex and allow fluid to flow out of vacuum chamber 310 along the wall of cylinder 308. Seal 312 flexes back to a sealing position on an expansion stroke, or when pressure is released on a compression stroke.

Piston 302 can reciprocate within cylinder 308 between a compressed position (as illustrated in FIG. 3A) and an expanded position (as illustrated in FIG. 3B). An elastic member such as piston spring 304 can be operably associated with piston 302 to bias piston 302 toward the expanded position. For example, a first end of piston spring 304 may abut or otherwise engage a first end of cylinder 308, and a second end of piston spring 304 may abut or otherwise engage piston spring 304, either directly or indirectly through seal 312 (as illustrated in FIGS. 3A-3B).

In operation, port 314 may be fluidly coupled to a charging chamber, such as charging chamber 202. To reduce pressure in the charging chamber, piston 302 can be moved to the compressed position, which decreases the volume of vacuum chamber 310. Seal 312 allows fluid within vacuum chamber 310 to exit during the compression stroke. After moving piston 302 to the compressed position, piston spring 304 exerts a force on seal 312 that attempts to return piston 302 to the expanded position, which increases the volume of vacuum chamber 310. As the volume of vacuum chamber 310 increases, seal 312 prevents fluid from entering vacuum chamber 310, which reduces the pressure in vacuum chamber 310. The pressure between vacuum chamber 310 and the charging chamber can be equalized through port 314, which results in a pressure reduction in the charging chamber. After piston 302 has moved to an expanded position, piston 302 may be moved again to a compressed position to recharge the charging chamber.

Piston-driven pump 300 may be manually-actuated, or may be actuated by an electrical, hydraulic, or pneumatic actuator, for example. For all of the charging chambers described herein, pressure may be reduced by manual or electrically powered means. In some embodiments, for example, charging chamber 202 may initially be charged or re-charged to a selected reduced pressure by a reduced pressure pump or a vacuum pump driven by an electric motor. In another illustrative embodiment, a wall suction unit (such as are commonly available in hospitals and other medical facilities) may be used to reduce pressure in charging chamber 202 to a selected pressure.

Figure 4A:
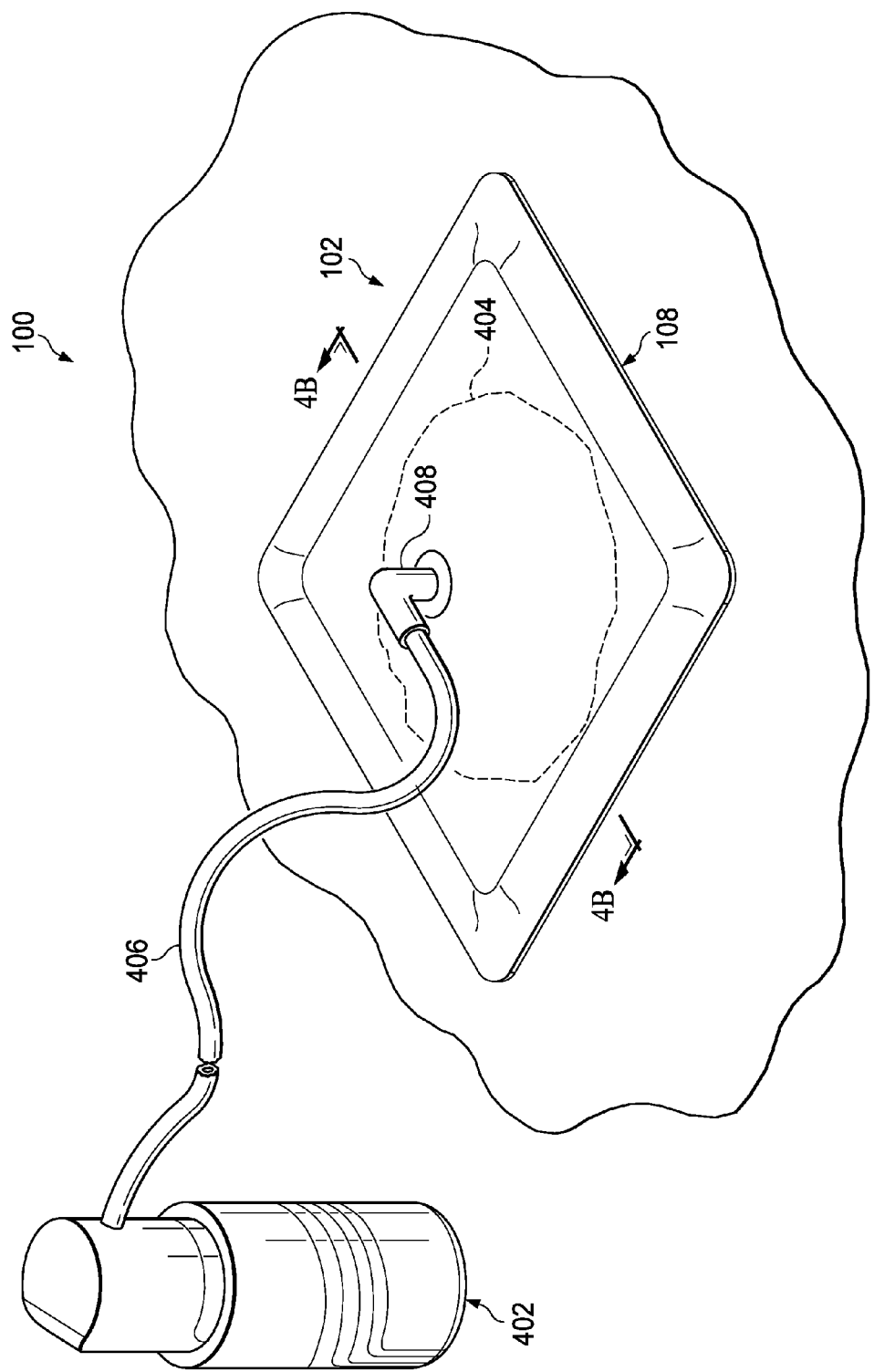
FIG. 4A is a perspective view of an example embodiment of the reduced pressure therapy system.

FIG. 4A is a perspective view of an illustrative embodiment of reduced-pressure therapy system 100. In this example embodiment, the reduced-pressure source is a vacuum pump 402 that may be manually operated. Dressing 102 may be positioned at a tissue site 404, and includes drape 108 adapted for sealing around tissue site 404. Dressing 102 may be fluidly coupled to vacuum pump 402 through a tube 406, which may be a multi-lumen tube. Tube 406 may fluidly communicate with dressing 102 through an adapter 408, as illustrated, or through one or more apertures in dressing 102.

Figure 4B:
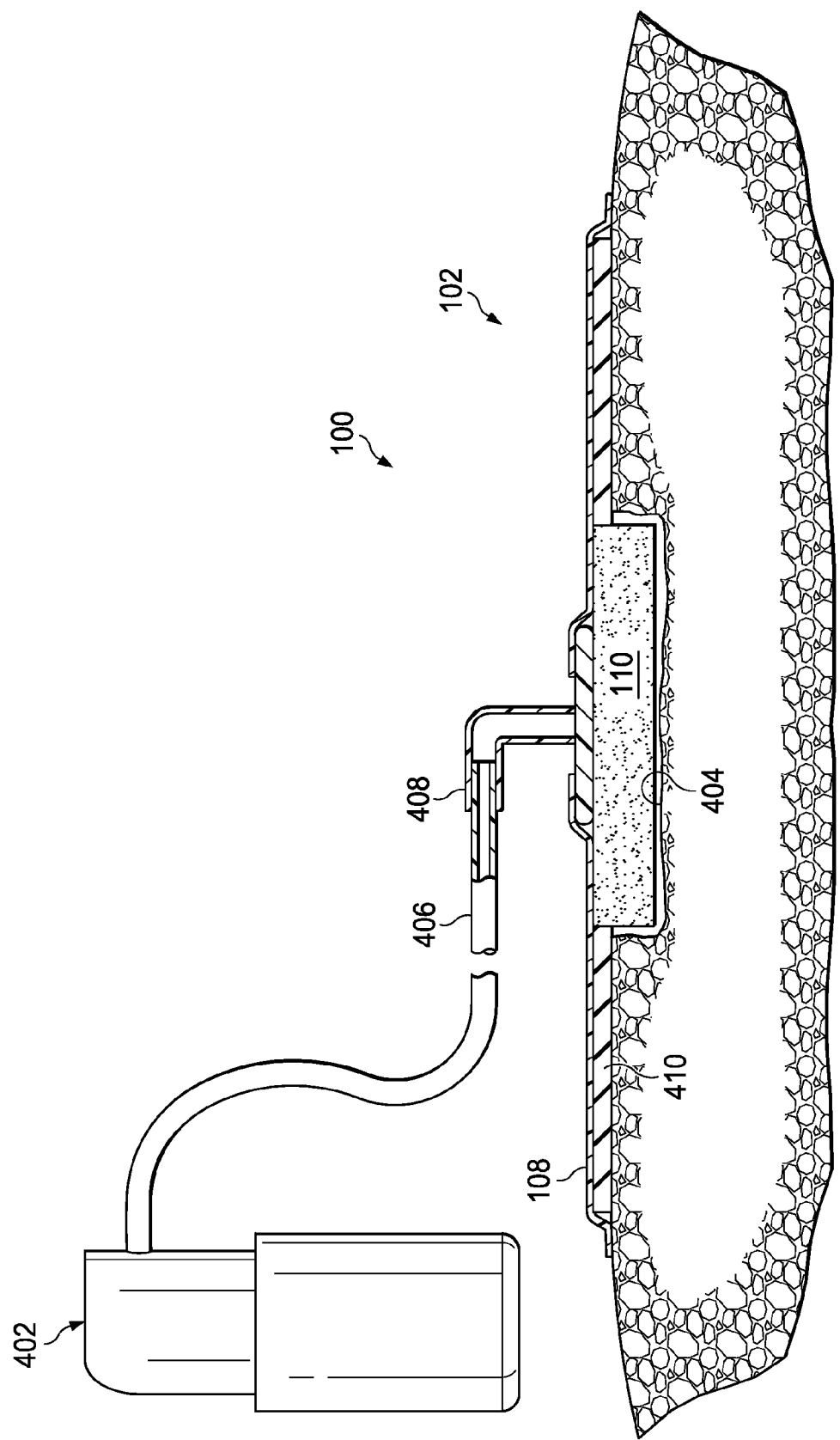
FIG. 4B is a partial cross-sectional view of the example embodiment of the reduced-pressure therapy system in FIG. 4A taken along line 4-4.

FIG. 4B is a partial cross-sectional view of the example embodiment of reduced-pressure therapy system 100 in FIG. 4A taken along line 4-4, which illustrates additional details that may be associated with certain embodiments. In such embodiments, dressing 102 may include pressure distribution manifold 110 and a sealant 410. In operation, pressure distribution manifold 110 may be positioned within, over, on, or otherwise proximate to tissue site 404, sealant 410 may be applied to drape 108 or to epidermis surrounding tissue site 404, and drape 108 may be placed over pressure distribution manifold 110. Sealant 410 may be activated or engaged to provide a sealing layer between drape 108 and epidermis surrounding tissue site 404 (preferably undamaged epidermis). Thus, drape 108 encloses pressure distribution manifold 110 and tissue site 404 in a sealed therapeutic environment in which pressure may be controlled.

Figure 5:
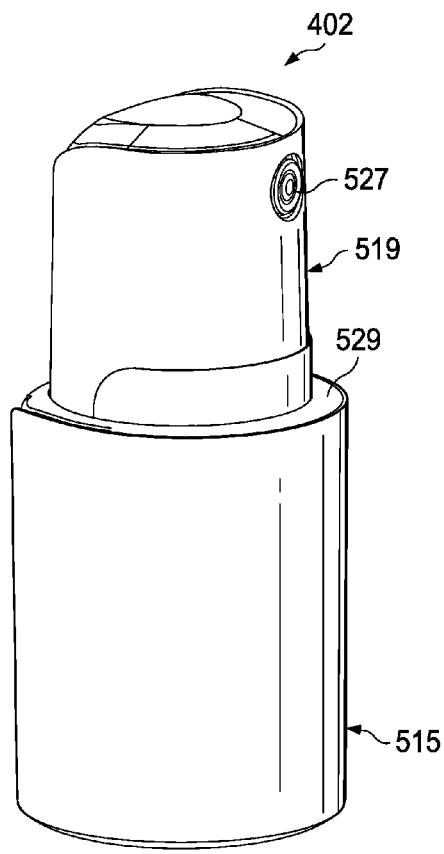
FIG. 5 is a perspective view of a vacuum pump that may be associated with some embodiments of the reduced-pressure therapy system.
Figure 6:
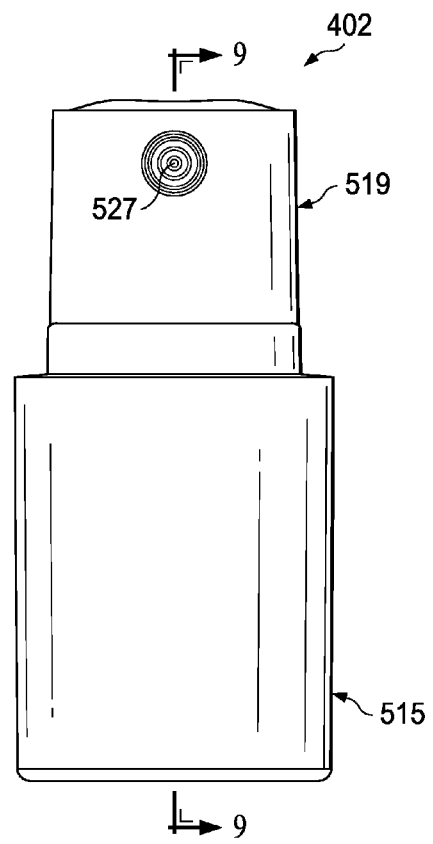
FIG. 6 is a front view of the vacuum pump illustrated in FIG. 5.

FIG. 5 is a perspective view of vacuum pump 402 illustrating additional details that may be associated with some embodiments. FIG. 6 is a front view of the embodiment of vacuum pump 402 illustrated in FIG. 5. In these illustrative embodiments, vacuum pump 402 generally includes a first barrel 515 and a second barrel 519. While first barrel 515 and second barrel 519 are illustrated as having substantially cylindrical shapes, the barrels could be other shapes that permit operation of the device. First barrel 515 may be an outer barrel having an interior dimension greater than an exterior dimension of second barrel 519, which may be an inner barrel.

Referring to FIGS. 5-9, first barrel 515 may include a closed end, an adjoining side wall, and an open end opposite the closed end. A cavity, such as cylinder 523 may be defined generally by the side wall. Cylinder 523 may slidingly receive second barrel 519 through the open end of first barrel 515, and second barrel 519 can be movable between an extended position and a compressed position. Vacuum pump 402 may additionally include a barrel ring 529 and two pistons, referred to as piston 531 and seal 535. Barrel ring 529 may be positioned at the open end of first barrel 515 to circumscribe second barrel 519. Barrel ring 529 can eliminate large gaps between first barrel 515 and second barrel 519 at an open end of first barrel 515. Piston 531 and seal 535 may be slidingly received within cylinder 523 of first barrel 515. Both piston 531 and seal 535 can be positioned in cylinder 523 between second barrel 519 and a closed end of first barrel 515, seal 535 being positioned between second barrel 519 and piston 531.

Figure 9:
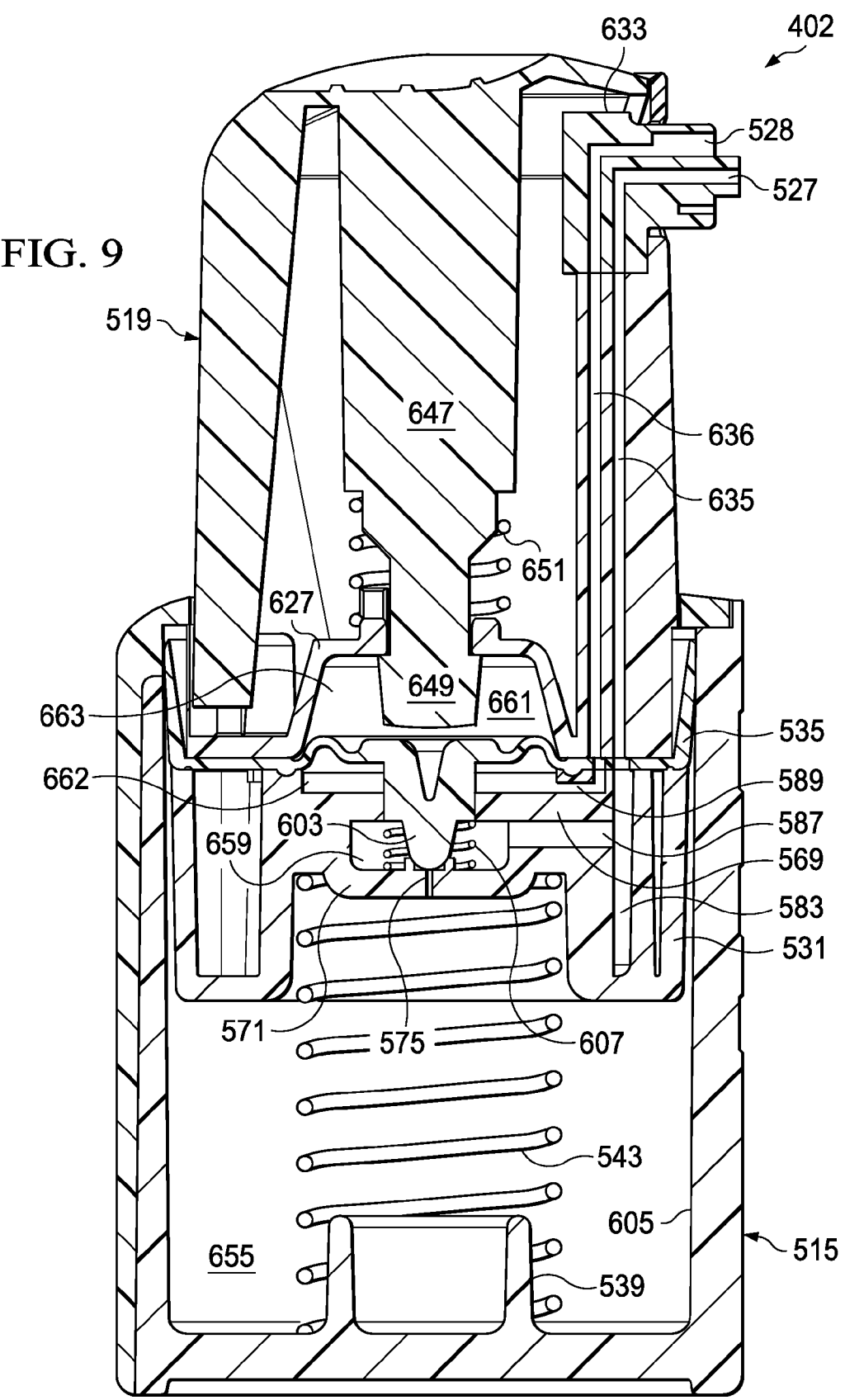
FIG. 9 is a cross-sectional side view of the vacuum pump of FIG. 6 taken at 9-9.

Referring more specifically to FIG. 9, first barrel 515 may include a protrusion 539 extending from the closed end of first barrel 515 toward the open end of first barrel 515. An elastic member, such as charging spring 543, can be positioned within first barrel 515. Protrusion 539 can receive one end of charging spring 543, which can reduce lateral movement of charging spring 543 within cylinder 523. An opposite end of charging spring 543 can be received against piston 531. Charging spring 543 can bias piston 531, seal 535, and second barrel 519 toward the expanded position.

Figure 10:
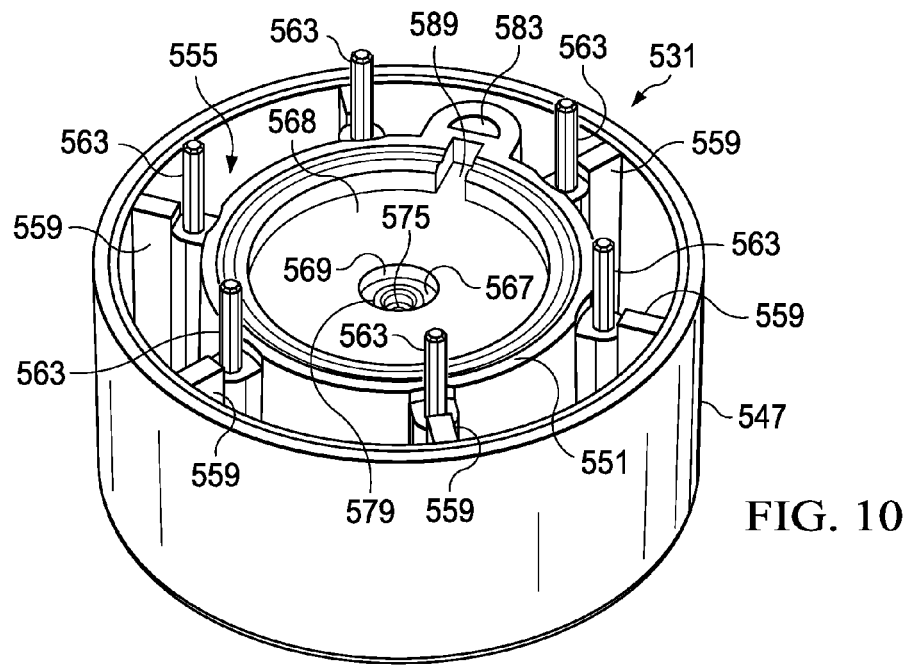
FIG. 10 is a top-rear perspective view of a piston of the vacuum pump of FIG. 5.
Figure 11:
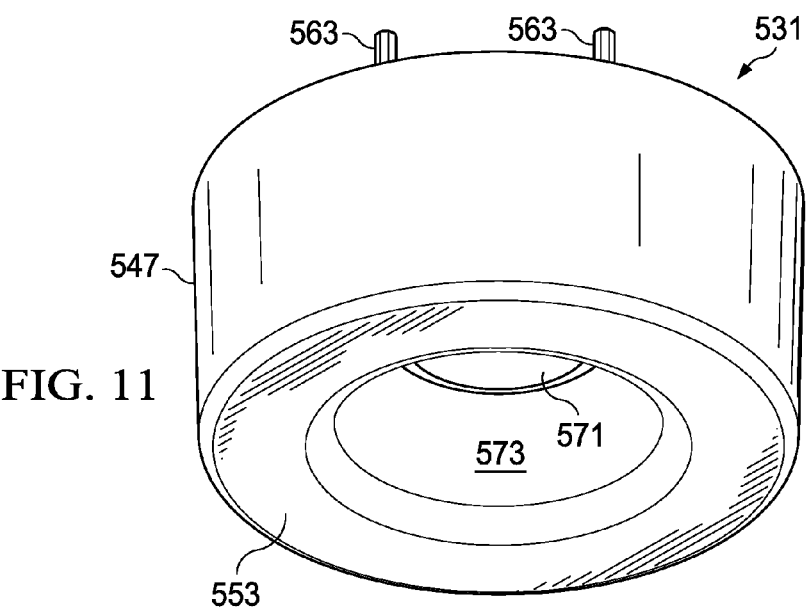
FIG. 11 is a bottom-rear perspective view of the piston of FIG. 10.

Referring again to FIGS. 7-9, but also to FIGS. 10 and 11, piston 531 in this example embodiment generally includes an outer wall 547 and an inner wall 551 joined by an outer floor 553. An annulus 555 may be disposed between outer wall 547 and inner wall 551, and a plurality of radial supports 559 can be positioned between outer wall 547 and inner wall 551 in annulus 555. Radial supports 559 can provide additional rigidity to piston 531, while reducing the weight of piston 531 relative to a single-wall piston that includes no annulus. However, a single-wall piston, a double-wall piston, or other variations may be suitable for various applications.

A plurality of guides 563 can be disposed on piston 531, and in one embodiment, one of guides 563 may be disposed on each radial support 559. Guides 563 can align piston 531 relative to seal 535 and second barrel 519. Guides 563 can further serve to secure piston 531 to second barrel 519 by means of a friction fit.

In the illustrated embodiment, piston 531 further includes a lower bowl 567 defined by inner wall 551, a partition 569, and an inner floor 571. Piston 531 may also include an upper bowl 568, generally defined by inner wall 551 and partition 569, wherein lower bowl 567 and upper bowl 568 are disposed on opposing sides of partition 569. In one embodiment, inner floor 571 may be two-tiered or multi-tiered, but inner floor 571 may instead be single-tiered and/or substantially planar. Inner floor 571 may also be positioned such that a recess 573 is defined beneath inner floor 571 to receive an end of charging spring 543 (see FIGS. 9 and 11). A charging port 575 may pass through inner floor 571. A valve seat 579 may be positioned in lower bowl 567 near charging port 575 such that fluid communication through charging port 575 may be selectively controlled by selective engagement of valve seat 579 with a valve body.

A well 583 may also be positioned in annulus 555 of piston 531, and a channel 587 can fluidly connect well 583 and lower bowl 567. Channel 587 can allow fluid communication between well 583 and lower bowl 567.

Figure 7:
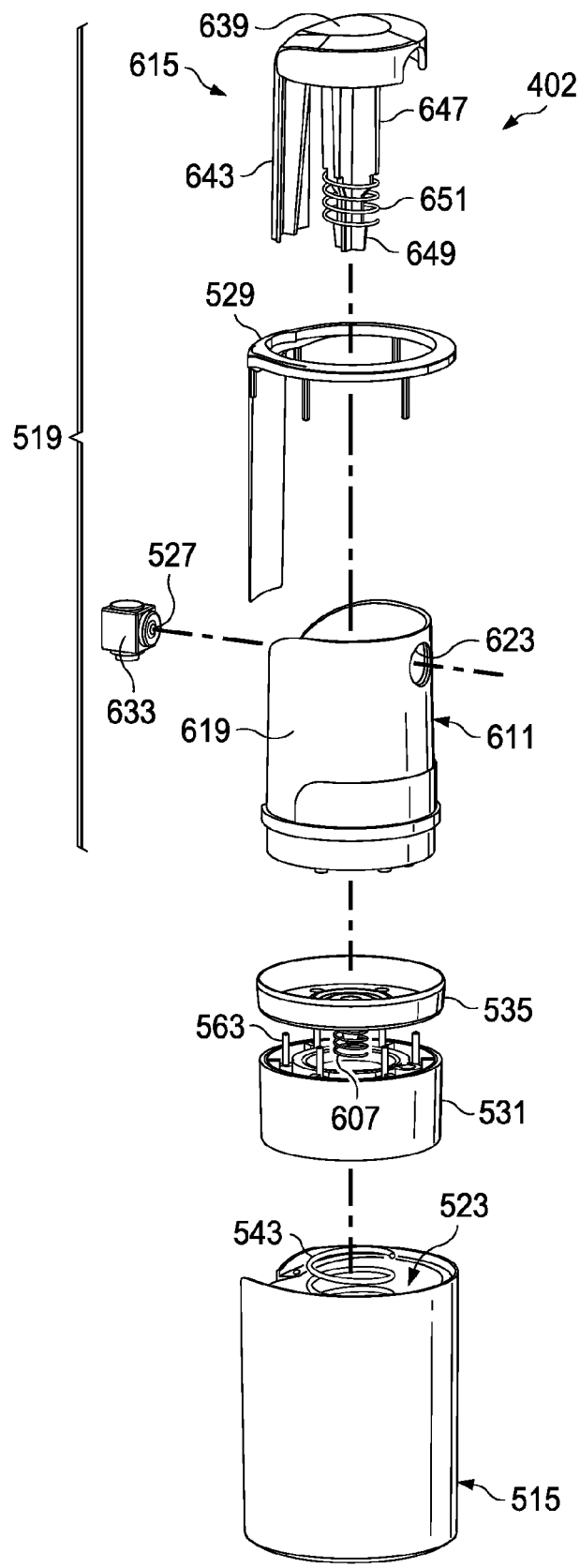
FIG. 7 is an exploded side perspective view of the vacuum pump of FIG. 5.
Figure 8:
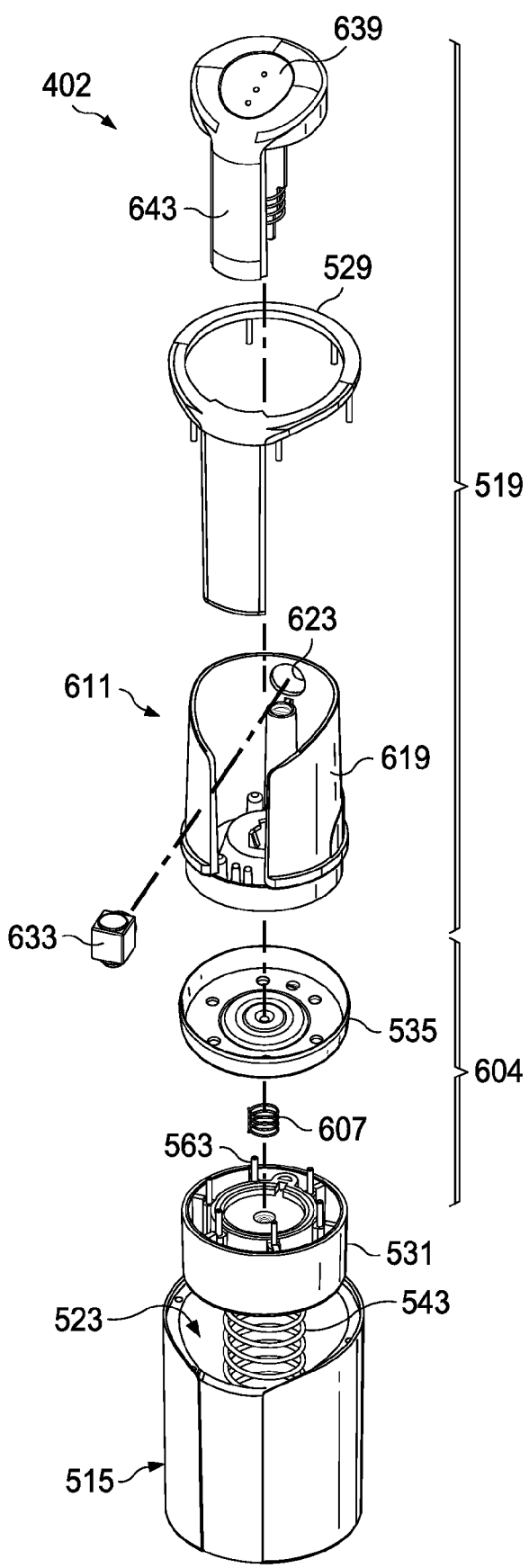
FIG. 8 is an exploded rear perspective view of the vacuum pump in FIG. 5.

Referring still to FIGS. 7-9, but also to FIGS. 12 and 13, seal 535 may include a central portion 591 circumscribed by a skirt portion 595. A plurality of guidance apertures 599 can be disposed in central portion 591 to receive guides 563 of piston 531 when vacuum pump 402 is assembled. A multi-channel aperture, such as communication aperture 601, may be similarly disposed in central portion 591, and in one embodiment, communication aperture 601 can be located at a distance from a center of seal 535 equal to the distance of guidance apertures 599 from the center. Communication aperture 601 can permit fluid communication through central portion 591 of seal 535.

Skirt portion 595 of seal 535 extends axially from an edge of central portion 591. As illustrated in FIG. 9, skirt portion 595 can engage an inner surface 605 of first barrel 515 to permit unidirectional fluid communication past seal 535. In other words, skirt portion 595 of seal 535 can allow fluid to flow past skirt portion 595 if the fluid flow is directed from the side of seal 535 on which piston 531 is disposed toward the opposite side of seal 535. Skirt portion 595, however, substantially prevents fluid flow in the opposite direction. While the skirt portion 595 of seal 535 effectively controls fluid communication past skirt portion 595, a valve member such as, for example, a check valve or other valve could instead be used to perform this function.

As illustrated in more detail in FIGS. 9 and 13, a valve body 603 may be coupled to, abut, or otherwise engage central portion 591 of seal 535. Although valve bodies of many types, shapes and sizes may be used, valve body 603 in this illustrative embodiment can be generally conical with an apex 609 adapted to sealingly engage valve seat 579 of piston 531. While valve body 603 is illustrated as being an integral part of seal 535 in this example, valve body 603 may alternatively be a separate component from seal 535 that is provided to engage valve seat 579.

In one embodiment, both seal 535 and valve body 603 can be made from an elastomeric material, such as a medical grade silicone, for example. While many different materials may be used to construct, form, or otherwise create seal 535 and valve body 603, a flexible material can improve the sealing properties of skirt portion 595 with inner surface 605 and valve body 603 with valve seat 579.

Figure 18:
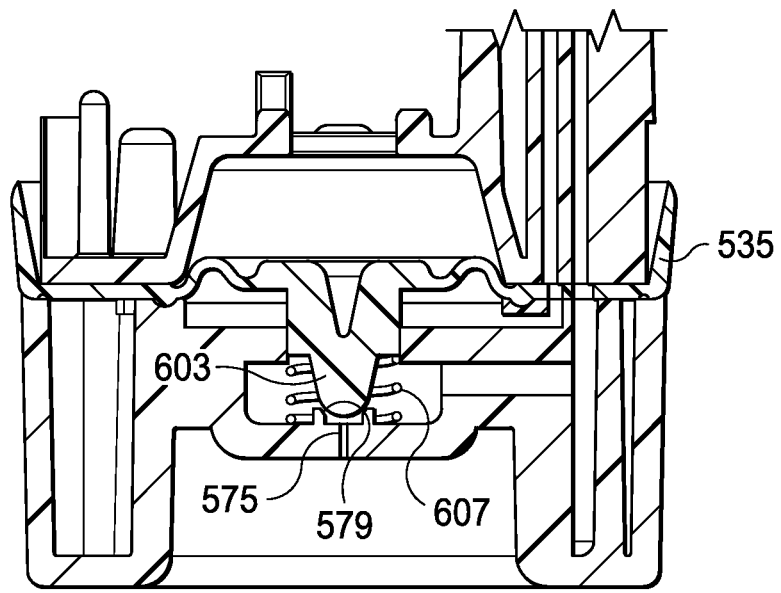
FIG. 18 is an enlarged cross-sectional view of the vacuum pump of FIG. 17.

Referring more specifically to FIG. 9, a regulator spring 607 can be disposed between seal 535 and charging port 575 to bias valve body 603 away from charging port 575. For example, one end of regulator spring 607 may be positioned concentrically around valve seat 579 within lower bowl 567 of piston 531, while another end of regulator spring 607 may engage a shoulder of valve body 603. Regulator spring 607 generally biases regulator valve 604 toward an open position, in which valve body 603 may be disengaged from port 575 and valve seat 579 to permit fluid communication through charging port 575. In one example embodiment, only central portion 591 of seal 535 moves due to the flexibility of the seal 535 (see FIG. 18). In another embodiment, regulator spring 607 may move seal 535 in its entirety.

Figure 14:
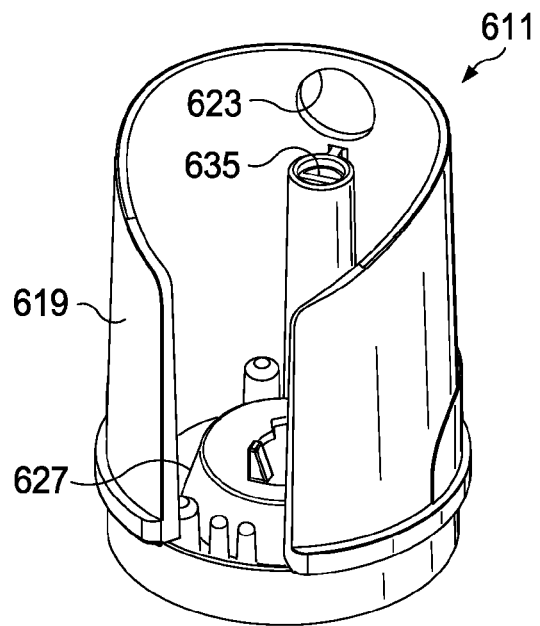
FIG. 14 is a top-rear perspective view of a second barrel of the vacuum pump of FIG. 5.
Figure 15:
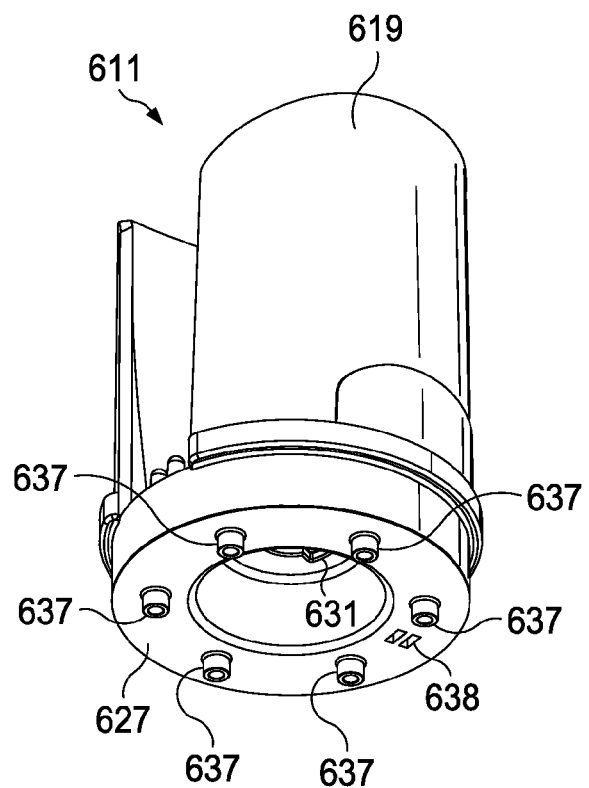
FIG. 15 is a bottom-rear perspective view of the second barrel of FIG. 14.

Referring again to FIGS. 7-9, but also to FIGS. 14 and 15, an example embodiment of second barrel 519 includes a first housing portion 611 and a second housing portion 615. First housing portion 611 can include an outer shell 619 having an aperture 623, which may be disposed near an open end of first housing portion 611, for example. A floor 627 may be integrally formed with or otherwise connected to outer shell 619 on an end of first housing portion 611 opposite the open end. An aperture 631 may be centrally disposed in floor 627. A boss 633 can be integrated with or connected to first housing portion 611. Boss 633 may include supply port 527, which can be physically aligned with aperture 623 to allow a tube to be fluidly connected to supply port 527 through aperture 623. One embodiment of boss 633 is a ninety degree fluid fitting that can couple supply port 527 to a fluid channel 635 positioned within first housing portion 611, and can couple a control port 528 to a fluid channel 636. Fluid channel 635 and fluid channel 636 may be, for example, rigid conduits formed from the same or similar material as that of outer shell 619, or in alternative embodiments, fluid channel 635 and fluid channel 636 may be lumina in a flexible, multi-lumen conduit.

Referring more specifically to FIG. 15, a plurality of guidance apertures 637 can be disposed in floor 627 of first housing portion 611. A multi-channel aperture, such as communication aperture 638, may also be disposed in first housing portion 611, such as to allow fluid communication through floor 627. Guidance apertures 637 can receive guides 563 of piston 531, for example, to align communication aperture 638 with communication aperture 601. In one illustrative embodiment, a first channel of communication aperture 638 may also be aligned with fluid channel 635 and a second channel may be aligned with fluid channel 636, for example. A friction fit between guides 563 and guidance apertures 637 can also assist in securing the relative positions of piston 531 and second barrel 519. It should be readily apparent, however, that piston 531 and second barrel 519 may be secured by alternative means.

Second housing portion 615 may include an end cap 639 integrally or otherwise connected to a guide 643. Together, end cap 639 and guide 643 may slidingly engage outer shell 619 of first housing portion 611 to create a substantially closed second barrel 519 (with the exception of various apertures and passages). While second barrel 519 may be constructed from fewer components, the existence of first housing portion 611 and second housing portion 615 can allow easier access within second barrel 519 and easier assembly of vacuum pump 402.

In certain example embodiments, a shaft 647 may extend from end cap 639 and can include an engagement end 649 opposite end cap 639. When second barrel 519 is assembled, shaft 647 may be substantially coaxial with a longitudinal axis of second barrel 519 and extend through aperture 631 in floor 627 of first housing portion 611. An elastic member such as spring 651 may be positioned within second barrel 519 such that one end of spring 651 bears upon floor 627 of first housing portion 611 and another end of spring 651 bears upon shaft 647 or another portion of second housing portion 615. Spring 651 can bias shaft 647 and other portions of second housing portion 615 toward a disengaged position (see position of shaft 647 in FIG. 9) in which engagement end 649 of shaft 647 does not bear upon seal 535 or valve body 603. A sliding relationship and engagement between first housing portion 611 and second housing portion 615 allows a force to be exerted on second housing portion 615 (against the biasing force of spring 651) to move second housing portion 615 to an engaged position. In the engaged position, engagement end 649 of shaft 647 can bear upon seal 535 above valve body 603 (see FIG. 16), which forces valve body 603 against valve seat 579, thereby substantially reducing or preventing fluid communication through charging port 575.

When vacuum pump 402 is assembled as illustrated in FIG. 9, for example, a charging chamber 655 can be generally defined by a sealed portion of cylinder 523 between piston 531 and the closed end of first barrel 515. A supply chamber 659 may be generally defined beneath partition 569, within lower bowl 567 of piston 531. A control chamber 661 can be generally defined between upper bowl 568 of piston 531 and floor 627 of first housing 611. Seal 535 can be disposed at least partially within control chamber 661 to divide control chamber 661 into a region of control pressure 662 and a region of ambient pressure 663. A port such as charging port 575 can allow fluid communication between charging chamber 655 and supply chamber 659 depending on the position of valve body 603. Supply chamber 659 can fluidly communicate with well 583 of piston 531 through fluid channel 587, and control chamber 661 may fluidly communicate with fluid channel 636 through channel 589. Well 583 can be aligned with communication aperture 601 of seal 535 and communication aperture 638 of first housing portion 611, which can allow fluid communication between well 583, fluid channel 635, and supply port 527 of second barrel 519.

While charging port 575 is illustrated as being disposed within piston 531 in this example, charging port 575 could instead be routed through the wall of first barrel 515. Charging port 575 could be any conduit or passage suitable for allowing fluid communication between the chambers.

In operation, vacuum pump 402 can be used with other components of a reduced pressure treatment system similar to those of reduced pressure treatment system 100. Supply port 527 of vacuum pump 402 can be adapted to be connected to a delivery tube or other conduit, for example, which may be fluidly connected to a tissue site. Although a fluid container could be integrated into vacuum pump 402, in some embodiments, vacuum pump 402 may not be intended to collect wound exudates or other fluids within an internal chamber. In certain embodiments, vacuum pump 402 may either be used with low-exudating wounds, or an alternative collection system such as an external canister or absorptive dressing may be used to collect fluids.

Figure 16:
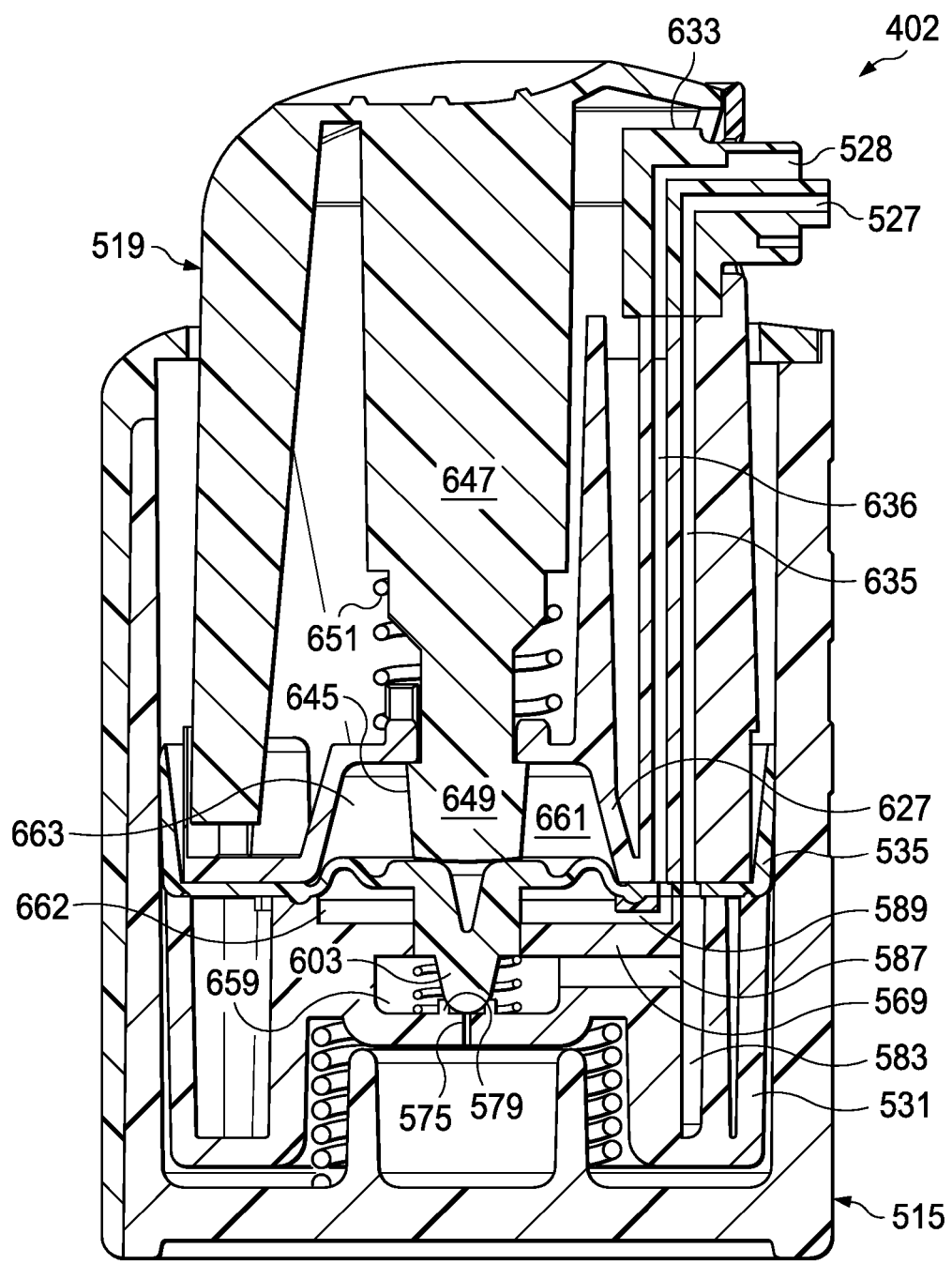
FIG. 16 is a cross-sectional side view of the vacuum pump of FIG. 5.

Referring to FIGS. 9 and 16, an expanded position (see FIG. 9) and a compressed position (see FIG. 16) of vacuum pump 402 are illustrated. In an initial state, vacuum pump 402 may be in an expanded position and not "charged" with reduced pressure. To charge vacuum pump 402, second barrel 519 can be manually compressed into first barrel 515 such that vacuum pump 402 is placed in the compressed position. As second barrel 519 compresses within first barrel 515 and moves toward the closed end of first barrel 515, the force being exerted on second barrel 519 can be generally transmitted to seal 535 and piston 531. The movement of second barrel 519, seal 535, and piston 531 into the compressed position decreases the volume of charging chamber 655. As the volume of charging chamber 655 decreases, pressure in charging chamber 655 increases and seal 535 flexes to permit air and other gases within charging chamber 655 to exit past skirt portion 695.

If the compressive force exerted upon second barrel 519 is removed, the biasing force exerted by charging spring 543 on piston 531 moves piston 531, seal 535, and second barrel 519 toward an expanded position. As this movement occurs, the volume of charging chamber 655 increases. Since skirt portion 595 of seal 535 allows only unidirectional flow, air and other gases are not permitted to enter charging chamber 655 past skirt portion 595. A reduction in pressure (i.e., a generation of reduced pressure) occurs within charging chamber 655 as the volume increases. The pressure reduction within charging chamber 655 is generally dependent on the size of charging chamber 655, range of motion of piston 531, properties of charging spring 543, and the integrity of seal 535. Thus, the pressure limits of charging chamber 655 may be controlled by adjusting these parameters. In some embodiments, for example, a range of motion of piston 531 may be calibrated at so that a complete stroke (i.e., compression and expansion) reduces pressure in charging chamber 655 below a prescribed therapy pressure. For example, if the prescribed therapy pressure is −125 mmHg, a range may be selected to reduce the pressure in charging chamber 655 to −150 mmHg.

In the example embodiment of vacuum pump 402, regulator valve 604 includes seal 535, valve body 603, and regulator spring 607. The operation of regulator valve 604 can be controlled by two forces acting primarily on seal 535. One of the forces is the result of a pressure differential between control pressure 662 and ambient pressure 663. The force resulting from the pressure differential may again be referred to as a "differential force." Regulator spring 607 also generally exerts another force on regulator valve 604. In expected operating ranges, the force of regulator spring 607 is directly proportional to the spring constant of regulator spring 607 and displacement of the ends of regulator spring 607 from a state of equilibrium. The force exerted by regulator spring 607 is generally in direct opposition to the direction of displacement. Thus, the differential force tends to compress regulator spring 607 if control pressure 662 is less than ambient pressure 663, and the force of regulator spring 607 in a compressed position opposes the differential force. The differential force and the force of regulator spring 607 can be combined to determine a net force acting on regulator valve 604.

Regulator valve 604 can leverage the differential force and the force of regulator spring 607 to regulate a therapy pressure that can be delivered to supply port 527 and a dressing applied to a tissue site. In some embodiments, regulator spring 607 may be tuned based on a prescribed therapy. For example, a spring constant may be selected based on a prescribed therapy pressure, or the compression of regulator spring 607 may be adjusted based on the prescribed therapy pressure. In one illustrative embodiments for example, first barrel 515 and second barrel 519 may be threaded so that second barrel 519 can be rotated to change the compression of regulator spring 607. Since changing the compression of regulator spring 607 changes the force of regulator spring 607 acting on valve body 603, the pressure differential required to actuate regulator valve 607 can also be changed.

Figure 17:
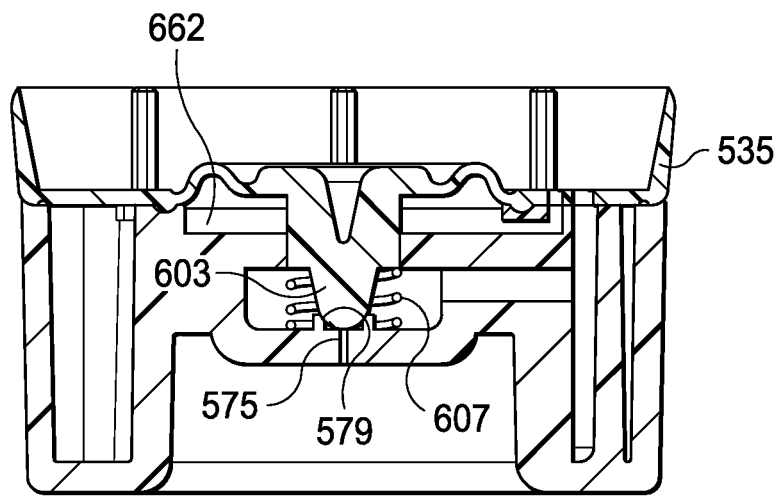
FIG. 17 is an enlarged cross-sectional view of the vacuum pump of FIG. 16.

Thus, if regulator spring 607 is calibrated to a particular therapy pressure and control pressure 662 in control chamber 661 is higher than the therapy pressure, the force of regulator spring 607 should exceed the differential force and move regulator valve 604 into an open position (see FIG. 18) in which valve body 603 disengages valve seat 579. If valve body 603 disengages valve seat 579, pressure between charging chamber 655 and supply chamber 659 can equalize through charging port 575. As the pressure in charging chamber 655 and supply chamber 659 continues to equalize, the pressure in supply chamber 659 continues to decrease. The pressure in the dressing also decreases as the pressure in supply chamber 659 and the pressure in the dressing equalize through supply port 527, unless there is a complete blockage in the fluid path between supply chamber 659 and the dressing. Likewise, control pressure 662 also decreases as control pressure 662 equalizes with the pressure in the dressing through control port 528, unless there is a complete blockage in the fluid path between the dressing and control chamber 661, which causes the differential force to increase. Thus, if control pressure 662 is reduced below the therapy pressure, the differential force should exceed the force of regulator spring 607 and move regulator valve 604 into the closed position (see FIG. 17) so that valve body 603 engages valve seat 579 and closes charging port 575.

When vacuum pump 402 is initially connected to a delivery tube and tissue site for treatment, it may be necessary to compress second barrel 519 within first barrel 515 more than once. As each compression stroke is completed, air and other gases may be pulled from the delivery tube and the tissue site until the pressure within the tube and at the tissue site begins to approach the desired therapy pressure.

If second barrel 519 is compressed within first barrel 515, second housing portion 615 can move relative to first housing portion 611 so that shaft 647 exerts a force on valve body 603 that holds valve body 603 in the closed position to prevent positively pressurized gas (such as gas from charging chamber 655) from entering supply chamber 659. Since shaft 647 remains engaged during the entire charging stroke of vacuum pump 402, the air within charging chamber 655 can be vented past seal 535 and not into supply chamber 659.

While in some embodiments of vacuum pump 402, first barrel 515, second barrel 519, piston 531, seal 535, and other components may be cylindrical, the size and/or shape of the components may be varied. Additionally, the relative positions of valve seat 579 and valve body 603 may be reversed such that valve body 603 is positioned below valve seat 579.

It should be apparent from the foregoing that systems, methods, and apparatuses having significant advantages has been described. While shown in only a few forms, the systems, methods, and apparatuses illustrated are susceptible to various changes, modifications, and uses encompassed within the claims that follow.

We claim:
1. A reduced-pressure treatment system comprising:
a dressing;
a supply chamber fluidly coupled to the dressing through a supply lumen;
a control chamber fluidly coupled to the dressing through a feedback lumen;
a charging chamber fluidly coupled to the supply chamber through a port; and
a regulator valve within the control chamber and operable to reciprocate within the control chamber to control fluid communication through the port based on a differential between a control pressure in the control chamber and a therapy pressure.

2. The reduced-pressure treatment system of claim 1, further comprising a reduced-pressure source fluidly coupled to the charging chamber.

3. The reduced-pressure treatment system of claim 1, wherein a first pressure in the charging chamber is less than a second pressure in the supply chamber.

4. The reduced-pressure treatment system of claim 1, wherein a first pressure in the charging chamber is less than a second pressure in the supply chamber, and the second pressure in the supply chamber is less than ambient pressure.

5. The reduced-pressure treatment system of claim 1, wherein the regulator valve comprises a piston and an elastic member adapted to bias the piston against ambient pressure in the control chamber.

6. The reduced-pressure treatment system of claim 1, wherein:
the control chamber is divided into a region of ambient pressure and a region of control pressure;
the feedback lumen is fluidly coupled to the region of control pressure; and
the regulator valve comprises a piston and an elastic member adapted to bias the piston against the ambient pressure.

7. The reduced-pressure treatment system of claim 1, wherein:
a piston divides ambient pressure from a region of the control pressure;
the feedback lumen is fluidly coupled to the region of control pressure; and
an elastic member is disposed in the control chamber and engaged to the piston.

8. The reduced-pressure treatment system of claim 1, wherein the supply lumen and the feedback lumen are disposed within a single tube fluidly coupled to the dressing.

9. The reduced-pressure treatment system of claim 1, wherein:
the supply lumen and the feedback lumen are disposed within a single tube fluidly coupled to the dressing;
the supply lumen is fluidly coupled to a first port in the supply chamber; and
the feedback lumen is fluidly coupled to a second port in the control chamber.

10. The reduced-pressure treatment system of claim 1, wherein:
the charging chamber comprises a piston opposing a closed end;
an elastic member is operably engaged to the piston;
the piston defines a wall of the supply chamber; and
the port is a passage through the piston.

11. The reduced-pressure treatment system of claim 1, wherein the control pressure is measured through the feedback lumen.

12. The reduced-pressure treatment system of claim 1, wherein the regulator valve comprises an elastic member calibrated to the therapy pressure.

13. The reduced-pressure treatment system of claim 1, wherein:
a piston divides an ambient pressure from the control pressure in the control chamber;

an elastic member is disposed in the control chamber and engaged to the piston to bias the piston against the ambient pressure;
the supply lumen and the feedback lumen are disposed within a single tube fluidly coupled to the dressing;
the supply lumen is fluidly coupled to a first port in the supply chamber;
the feedback lumen is fluidly coupled to the control pressure through a second port in the control chamber;
a first pressure in the charging chamber is less than a second pressure in the supply chamber, and
the second pressure in the supply chamber is less than the ambient pressure.

14. The reduced-pressure treatment system of claim 1, wherein the regulator valve comprises:
a piston;
a valve body coupled to the piston, the valve body movable with the piston to engage the port; and
an elastic member coupled to the valve body to bias the piston against ambient pressure in the control chamber.

* * * * *